United States Patent [19]

Myers

[11] E Patent Number: Re. 31,998

[45] Reissued Date of Patent: Oct. 8, 1985

[54] POSTERIOR CHAMBER LENS IMPLANT

[76] Inventor: William D. Myers, 5855 Wingcroft Ct., Birmingham, Mich. 48010

[21] Appl. No.: 587,955

[22] Filed: Mar. 9, 1984

Related U.S. Patent Documents

Reissue of:

[64] Patent No.: 4,412,359
Issued: Nov. 1, 1983
Appl. No.: 371,541
Filed: Apr. 26, 1982

[51] Int. Cl.[4] ..... A61F 1/16; A61F 1/24

[52] U.S. Cl. ..... 623/6

[58] Field of Search ..... 3/1, 13

[56] References Cited

U.S. PATENT DOCUMENTS

| | | | |
|---|---|---|---|
| 3,458,870 | 8/1969 | Stone, Jr. | 3/13 |
| 3,906,551 | 4/1975 | Otter | 3/13 |
| 4,074,368 | 2/1978 | Levy, Jr. et al. | 3/13 |
| 4,092,743 | 6/1978 | Kelman | 3/13 |
| 4,206,518 | 6/1980 | Jardon et al. | 3/13 |
| 4,242,760 | 1/1981 | Rainin | 3/13 |
| 4,244,060 | 1/1981 | Hoffer | 3/13 |
| 4,253,199 | 3/1981 | Banko | 3/13 |
| 4,365,360 | 12/1982 | Ong | 3/13 |

OTHER PUBLICATIONS

"Ridged Intraocular Lens May Lower Need for Discissions After Cataract Extraction", reprint from Ophthalmology Times, vol. 6, No. 4, Apr. 1981, (2 pages).

*Primary Examiner*—Ronald L. Frinks
*Attorney, Agent, or Firm*—Gifford, VanOphem, Sheridan, Sprinkle & Nabozny

[57] ABSTRACT

A posterior chamber lens implant is disclosed for use after extracapsular surgery. In extracapsular surgery the interior of the lens of the human eye is evacuated through a surgical opening formed in the front membrane of the lens while leaving the rear membrane of the lens or posterior capsule intact. The lens implant comprises an optic having a front surface and a rear surface and the implant is secured within the posterior chamber of the eye. In one form of the invention, a ridge spaces the rear surface of the optic forwardly from the posterior capsule while in a second form of the invention, the rear surface of the optic is concavely formed to space the rear surface of the optic forwardly of the posterior capsule. The implant of the present invention thus facilitates laser posterior capsulotomy in the event of clouding of the posterior capsule following the extracapsular surgery.

2 Claims, 6 Drawing Figures

POSTERIOR CHAMBER LENS IMPLANT

Matter enclosed in heavy brackets [ ] appears in the original patent but forms no part of this reissue specification; matter printed in italics indicates the additions made by reissue.

BACKGROUND OF THE INVENTION

I. Field of the Invention

The present invention relates to a posterior chamber lens implant for use after extracapsular surgery.

II. Description of the Prior Art

In extracapsular surgery, a surgical opening is formed through the front membrane or anterior capsule of the lens of the human eye and the cateracts and fluid within the interior of the lens is surgically removed. During such surgery, however, it is important to leave the posterior capsule of the lens intact so that it forms a barrier between the vitreous humor and the aqueous humor. Removal of the posterior capsule is known to result in a high incidence of retinal detachment as well as cystoid macular edema.

Following the removal of the cataracts, it is necessary to replace the human lens with an artificial lens implant in order to restore sight to the eye. Although these lens implants may be nested in the anterior chamber, i.e., behind the cornea, or in the pupil, it has been found that posterior chamber lens implants are medically superior to anterior chamber and pupil lens implants for a plurality of reasons.

The previously known posterior chamber lens implants comprise an optic having a convex front surface and generally planar rear surface. The lens implant is nested within the posterior chamber and so that the rear surface of the optic flatly abuts against the posterior capsule. The optic is typically secured in place in the posterior chamber by loops or haptics extending outwardly from the optic and sandwiched between the posterior capsule and anterior leads.

In a high incidence of cases, after a period of time following implantation of the lens the posterior capsule becomes clouded and obscures the vision of the eye. In order to restore the vision to the eye after this has occurred, it is necessary to perform a posterior capsulotomy to remove the portion of the posterior capsule that is aligned with the optic.

In one previously known method to perform a posterior capsulotomy known as discission, a needle is inserted into the eye and used to punch a hole through the posterior capsule and behind the optic. In many cases, however, the posterior capsule becomes tough following the extracapsular surgery so that it is necessary to enter the eye with scissors in order to cut a hole in the posterior capsule. Both discission and membrane cutting, however, involve a significant risk of introducing bacteria or other contaminants into the eye which may ultimately result in loss of the eye.

In the surgical procedure laser posterior capsulotomy, a laser is focused on the posterior capsule through the pupil. Upon activation of the laser, the laser burns an opening through the posterior capsule behind the optic thus restoring vision to the eye. The use of the laser in contrast with the previously known discission and membrane cutting is highly advantageous in that laser surgery is noninvasive and thus eliminates the possibility of introducing bacteria or other contaminants into the eye.

At present, however, laser posterior capsulotomy can be performed only on an anterior chamber or pupil lens implant. In a posterior chamber lens implant, the rear surface of the implant flatly abuts against the posterior capsule so that destruction of the posterior capsule by the laser may also result in destruction of the lens implant.

SUMMARY OF THE PRESENT INVENTION

The present invention provides a posterior chamber lens implant which enables a subsequent laser posterior capsulotomy to be performed, if necessary.

In brief, the lens implant of the present invention comprises an optic having a front surface, a rear surface and means for securing the optic within the posterior chamber. Preferably, the securing means comprises one or more haptics which are nested in between the posterior capsule and the anterior leads of the cataract capsule.

Unlike the previously known posterior chamber lens implant, however, the present invention comprises means for spacing the rear surface of the optic forwardly of the posterior capsule thus forming a space between the rear surface of the optic and the posterior capsule. In the preferred form of the invention, an annular ridge is formed around the outer periphery of the optic on its rear side so that the ridge extends rearwardly from the optic. Consequently, following implantation of the lens into the posterior chamber, the ridge abuts against the posterior capsule and spaces the rear suface of the optic forwardly from the posterior capsule.

In a second preferred embodiment of the invention, the rear surface of the lens implant is concavely formed so that, with the lens positioned within the posterior chamber, only the outer periphery of the rear side of the optic abuts against the posterior capsule. The remainder of the rear surface of the optic is spaced forwardly of the posterior capsule.

In practice, only a relatively small spacing, for example, one millimeter, is necessary between the rear surface of the lens implant and the posterior capsule in order to enable a laser posterior capsulotomy to be safely performed.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENTS OF THE PRESENT INVENTION

Figure 1:
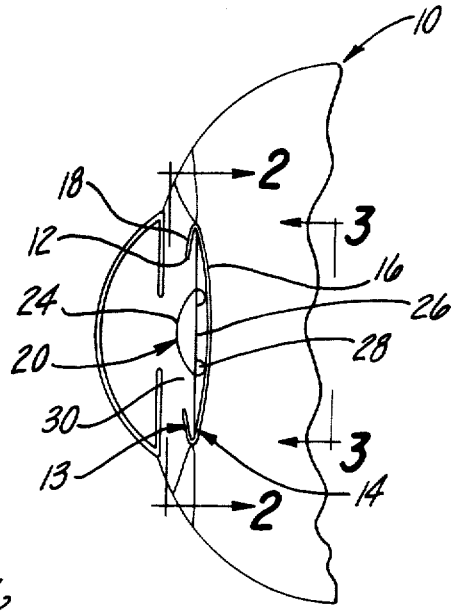
FIG. 1 is a fragmentary sectional view illustrating a first preferred embodiment of the lens implant of the present invention within the posterior chamber.
Figure 2:
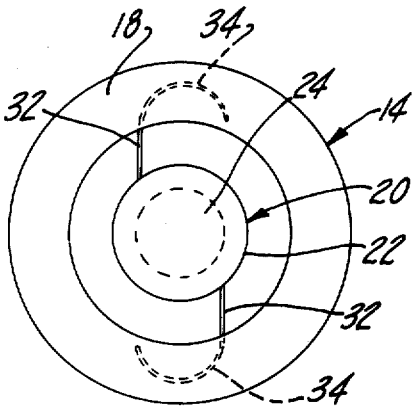
FIG. 2 is a fragmentary sectional view taken substantially along line 2—2 in FIG. 1.

With reference first to FIGS. 1 and 2, a human eye 10 is thereshown following extracapsular surgery. During extracapsular surgery, a circular opening 12 is formed in the anterior capsule 13 of the cataract capsule 14, or lens, and the cataracts are removed from the interior of the capsule 14. In doing so, the posterior capsule 16 of the lens 14 is left intact as well as an annular portion around the outer periphery of the anterior capsule 13 thus forming an annular anterior lead 18.

Figure 3:
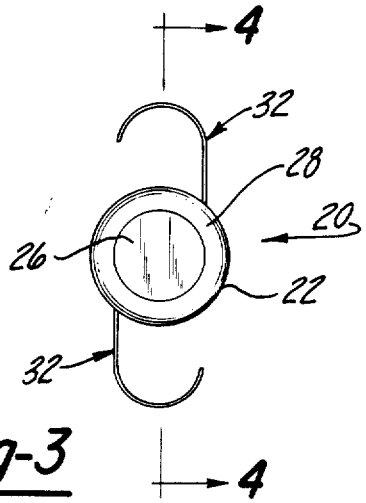
FIG. 3 is a view taken substantially along line 3—3 in FIG. 1 and with parts removed for clarity.

Referring now to FIGS. 1-3, a first preferred embodiment of the posterior chamber lens implant 20 of the present invention is thereshown and comprises a central optic 22 having a front convex surface 24 (FIG. 1) and a generally planar rear surface 26. The optic 22, which is typically constructed of plastic, is designed to reproduce or approximate the optical qualities of the lens of the human eye. *The optic is constructed of a material so that, with said optic implanted within the posterior chamber, said optic maintains a rigid shape following implantation.*

Figure 4:
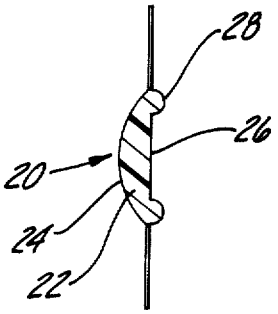
FIG. 4 is a sectional view taken substantially along line 4—4 in FIG. 3.
Figure 5:
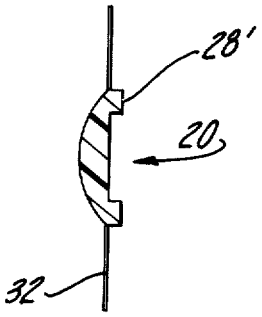
FIG. 5 is a view similar to FIG. 4 but showing a modification thereof.

As is best shown in FIGS. 3 and 4, an annular ridge 28 is formed around the outer periphery on the rear surface 26 of optic 22 so that the ridge 28 protrudes rearwardly from the optic 22. This ridge 28 is preferably continuous and integrally constructed with the optic 22. The ridge 28 illustrated in FIG. 4 is generally semicircular in cross sectional shape although other shapes, such as a square cross sectional shape as shown for the ridge 28' in FIG. 5, may alternatively be used.

With reference again to FIGS. 1 and 2, the lens implant 20 is positioned within the posterior chamber 30 of the eye 10 so that the ridge 28 flatly abuts against the posterior capsule 16. In doing so, the ridge 28 spaces the rear surface 26 of the optic 22 forwardly from the posterior capsule 16. This spacing, which is exaggerated in FIG. 1 for clarity, is preferably less than a few millimeters.

Any conventional means may be used to secure the lens implant 22 within the posterior chamber 30. However, as shown in the drawing, one or more haptics 32 are secured to and extend radially outwardly from the optic 22. A portion 34 of each haptic is positioned between the posterior capsule 16 and the anterior lead 18. Following extracapsular surgery, the anterior lead 18 folds against the posterior capsule 16 thus sandwiching the haptic portions 34 therebetween and securing the lens implant 20 in place. The use of haptics 32 positioned in between the posterior capsule 16 and anterior lead 18 is well known in the art.

Figure 6:
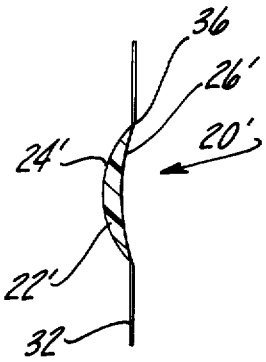
FIG. 6 is a view similar to FIGS. 4 and 5, but showing a second preferred embodiment of the invention.

With reference now particularly to FIG. 6, a still further preferred embodiment of the lens implant 20' is thereshown and comprises an optic 22' which is convex-o-concave in shape. As such, the optic 22' includes a front convex surface 24' and a rear concave surface 26'. Consequently, with the lens implant 20' positioned within the posterior chamber 30, only the outer periphery 36 of the optic 22' abuts against the posterior capsule 16 and spaces the central portion of the optic rear surface 26' forwardly from the posterior capsule 16.

It will be understood, of course, that still other constructions for the lens implant 20 may be used to space the rear surface 26 of the optic 22 forwardly from the posterior capsule 16.

By spacing the rear surface 26 of the optic 22 forwardly from the posterior capsule 16, the present invention enables the safe use of a laser to perform a posterior capsulotomy in the event that the posterior capsule subsequently becomes clouded or obscured. As previously described, unlike discission and membrane cutting, laser posterior capsulotomy completely eliminates the possibility of bacterial infection or the introduction of other contaminants into the eye.

Having described my invention, however, many modifications thereto will become apparent to those skilled in the art to which it pertains without deviation from the spirit of the invention as defined by the scope of the appended claims.

I claim:

1. A posterior chamber lens implant for a human eye for use after extracapsular surgery in which a posterior capsule is left substantially intact, said lens implant comprising:

a substantially circular rigid optic having a front surface, a rear surface and a substantially circular and continuous outer rear edge, said front surface being a continuous convex surface and said rear surface being a continuous concavely curved surface extending between said outer rear edge, means for securing said optic to the eye within the posterior chamber so that said outer rear edge abuts against the posterior capsule and so that the rear concavely curved surface of said optic is spaced from the posterior capsule by a distance sufficient to safely allow a subsequent laser posterior capsulotomy.

*2. A posterior chamber lens implant for a human eye for use after extracapsular surgery in which a posterior capsule is left substantially intact, said lens implant comprising:*

*a substantially circular optic having a front surface, a rear surface and a substantially circular and continuous outer rear edge, said front surface being a continuous convex surface and said rear surface being a continuous concavely curved surface extending between said outer rear edge,*

*means for securing said optic to the eye within the posterior chamber so that said outer rear edge abuts against the posterior capsule and so that the rear concavely curved surface of said optic is spaced from the posterior capsule by a distance sufficient to safely allow a subsequent laser posterior capsulotomy,*

*wherein said optic is constructed of a material so that, with said optic implanted within the posterior chamber, said optic maintains a rigid shape following implantation.*

* * * * *